United States Patent [19]

Sandstrom et al.

[11] 4,381,014

[45] Apr. 26, 1983

[54] RING ELECTRODE FOR PACING LEAD AND METHOD OF MAKING SAME

[75] Inventors: Richard D. Sandstrom, Scandia; Robert G. Dutcher, Columbia Heights; Keith A. Ufford, Maple Grove, all of Minn.

[73] Assignee: Medtronic, Inc., Minneapolis, Minn.

[21] Appl. No.: 195,987

[22] Filed: Oct. 10, 1980

[51] Int. Cl.³ .............................................. A61N 1/04
[52] U.S. Cl. ..................................................... 128/786
[58] Field of Search .............. 128/639, 784, 785, 786, 128/419 P

[56] References Cited

U.S. PATENT DOCUMENTS

| | | | |
|---|---|---|---|
| 3,348,548 | 10/1967 | Chardack | 128/419 P |
| 3,568,660 | 3/1971 | Crites | 128/786 |
| 3,837,347 | 9/1974 | Tower | 128/419 P |
| 4,156,429 | 5/1979 | Amundson | 128/419 P |
| 4,280,511 | 7/1981 | O'Neill | 128/784 |

*Primary Examiner*—William E. Kamm
*Attorney, Agent, or Firm*—Reed A. Duthler; Joseph F. Breimayer; John L. Rooney

[57] ABSTRACT

A structure for use as an electrode on a pacing lead to be located some distance proximal to the distal end of the pacing lead. Two short lengths of wire having high electrical conductivity are cut to size. The coils of the outer conductor are welded together at the desired location of the ring electrode of the lead. The two short lengths of wire are welded to the outer conductor of the lead at the desired location of the ring electrode. An insulating sheath having an inside diameter close to the outside diameter of the outer conductor is slid over the outer conductor. The flexibility of the insulating sheath is sufficient to permit encasing of the two short lengths of wire, though the insulating sheath is caused to protrude at the two places directly over and corresponding to the two short lengths of wire. A conductive ring having an inside diameter sufficient to permit sliding over the insulating sheath and two points of protrusion is placed around the insulating sheath at the desired location of the ring electrode. The conductive ring is swaged to an outside diameter approximating that of the insulating sheath. The forces produced cause the two short lengths of wire to pierce the insulating sheath and come in contact with the conductive ring which thereby creates an electrically conductive path between the outer conductor and the conductive ring.

17 Claims, 7 Drawing Figures

RING ELECTRODE FOR PACING LEAD AND METHOD OF MAKING SAME

CROSS REFERENCE TO COMMONLY ASSIGNED PATENT

Attention is drawn to commonly assigned U.S. Pat. No. 4,280,511 for "Ring Electrode for Pacing Lead and Process of Making Same" issued to Edward G. O'Neill on July 28, 1981, which is herewith specifically incorporated by reference.

BACKGROUND OF THE INVENTION

1. Field of the Invention

The present invention relates generally to a surgical electrode lead, and more specifically relates to a ring electrode for a pacing lead.

2. Description of the Prior Art

Though the ring electrode has many applications, the most prevalent is within one conducting path of a bipolar pacing lead. In the bipolar pacing lead, a first conductor terminates in a tip electrode at the distal end of the lead. A ring electrode is located a short distance proximal to the tip electrode and is connected to a second conductor of the bipolar pacing lead.

The problems experienced in fabricating and using the ring electrode are often practical ones. The earliest ring electrodes were welded to the corresponding conductor. Many leads fabricated today still use a welding technique. U.S. Pat. No. 3,348,548 issued to Chardack teaches welding of the ring electrode to the conductor. A problem with the weld technique is that the insulating sheath must be cut to permit electrical contact of the conductor and the ring electrode. If, as with present day leads, the conductor must be sealed from body fluids, the cuts must be sealed by molding or some other technique.

A second general technique for attachment of the ring electrode is via crimping. U.S. Pat. No. 3,769,984 issued to Muench teaches attachment of a ring electrode via crimp rings. As with the welding technique discussed above, the insulating sheath must be cut to permit contact between the conductor and the ring electrode. Muench teaches "dipping the material in a suitable adhesive material" to seal the cuts. Whereas this technique is usable, the sealing process represents an added step. The use of crimp rings is further complicated by the requirement to precisely position the conductor relative to the crimp ring.

SUMMARY OF THE INVENTION

The present invention provides a ring electrode that reliably seals the conductor from body fluids, while ensuring good electrical conduction and requiring fewer assembly steps than found in the prior art. The overall strength of the lead is enhanced through the use of a single piece of tubing. The coils of the lead conductor are welded together at the desired location of the ring electrode. Two short lengths of high conductivity wire are cut to length. The wires are permanently attached to the corresponding conductor by welding or other low electrical resistance technique. The two wires are spaced about 180° apart on the conductor. An insulating sheath is slid over the conductor and attached wires. The insulating sheath has deforming protrusions corresponding to the two attached wires.

The ring electrode is slipped over the insulating sheath. To accomplish this, the inside diameter of the ring electrode must be greater than the outside diameter of the insulating sheath containing the protrusions created by the attached wires. After properly locating the ring electrode directly covering the attached wires, the ring electrode is swaged to have an outside diameter approximating the outside diameter of the insulating sheath. The insulating sheath is thereby compressed, sealing the junction of the ring electrode and the insulating sheath. The compression causes the attached wires to penetrate the insulating sheath and come into contact with the ring electrode. The connection thus made is reliably maintained by the compression of the ring electrode against the welded conductor coil and attached wires. Strength of the assembly is maintained by the welded coils. When the lead is stretched, the outside diameter of the welded coils remains the same because they do not stretch. Therefore, the mechanical connection of the ring electrode and coil is sustained.

DETAILED DESCRIPTION OF THE PREFERRED EMBODIMENT

The preferred embodiment of the present invention uses a ring electrode as part of a bipolar lead for cardiac pacing. The ring electrode is positioned a short distance proximal of the distal end of the bipolar lead which contains the other electrode. For ease of understanding, the present description and drawings primarily disclose the important features of the present invention with only cursory attention to the features of the bipolar lead known in the art. Should the reader care to review the entire structure of current bipolar leads, it is recommended that U.S. Pat. Nos. 4,046,151 issued to Rose and 4,135,518 issued to Dutcher which are herein incorporated by reference, be consulted.

Figure 1:
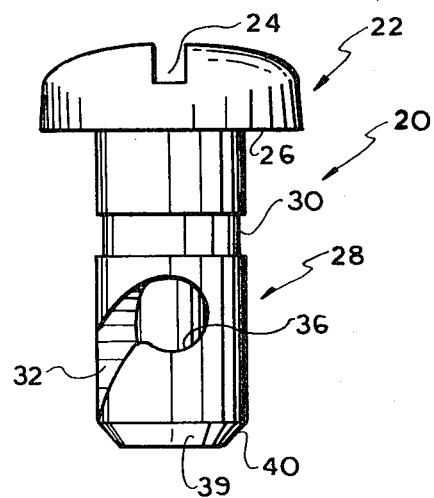
FIG. 1 is a top view of a portion of a bipolar pacing lead containing the preferred embodiment of the ring electrode.

FIG. 1 is a top view of a portion of the bipolar pacing lead containing a ring electrode in accordance with the present invention. Insulating sheath 10 covers the entire outer surface of the bipolar pacing lead except for the electrodes and the connector pins (not shown). Ring electrode 20 is exposed to permit electrical contact with surrounding tissue. Ring electrode 20 is made of platinum/iridium or other suitable conductive material which is substantially inert to body fluids and tissue. Ring electrode 20 has an outside diameter approximately the same as insulating sheath 10, thereby easing transvenous insertion. One of the two attached wires 22 is shown in dashed lines.

Figure 2:
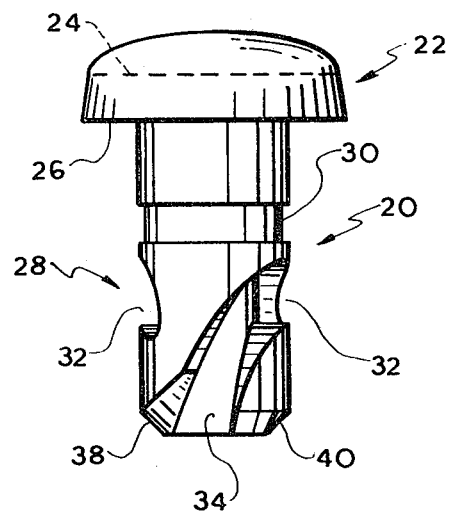
FIG. 2 is a side sectional view of the ring electrode as completely assembled.

FIG. 2 is a sectional view of the portion of the bipolar pacing lead containing ring electrode 20. Conductor 12 is located within insulating sheath 10. Care must be exercised that conductor 12 has low electrical resistance, great tensile strength and maximum flexibility. For that reason, materials chosen for conductor 12 (e.g. MP35N/Silver) are not usually impervious to body fluids and, therefore, must be sealed from the implanted environment by sheath 10. Conductor 12 is normally a tightly wound helix as shown to add flexibility. A second insulated conductor (not shown) may be inserted coaxially within conductor 12.

Wires 22 and 23 are permanently affixed to conductor 12 in a manner providing high electrical conductivity at contact positions 24 and 25. Wires 22 and 23 are highly conductive and must be resilient. Wires 22 and 23 penetrate insulating sheath 10 along their length at 26 and 27. Wires 22 and 23 provide electrical contact with ring electrode 20 along their length at 30 and 31. The seal between ring electrode 20 and insulating sheath 10 is effected at seal points 46, 47, 48 and 49.

Figure 3:
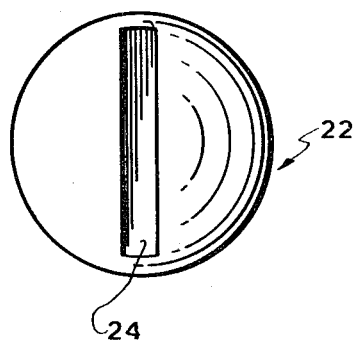
FIG. 3 is a similar view before installation of the insulating sheath after the wires are attached.

FIG. 3 provides a sectional view of conductor 12 with wires 22 and 23 attached. Wires 22 and 23 are short lengths (approximately 2.5 mm) of MP35N alloy. Wires 22 and 23 have a diameter of about 0.23 mm. Conductor 12 is a coil of conducting wire common in the art. Before wires 22 and 23 are attached, however, the coils of conductor 12 to be directly adjacent wires 22 and 23 are welded together at points 24 and 25. This causes conductor 12 to approximate a rigid cylinder at the place to which the ring electrode is to be attached. Wires 22 and 23 are then welded at some of the points 24 and 25 using laser or resistive techniques. Most important is that when attached, wires 22 and 23 are rigidly affixed and electrical resistance is minimized.

Figure 4:
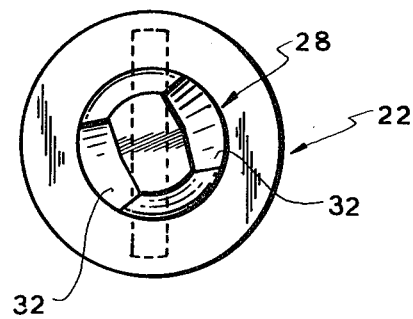
FIG. 4 is a top view of the wires attached to the conductor without insulating sheath.

FIG. 4 is a top view of conductor 12 with wire 22 attached. Notice that wire 22 is attached parallel to the longitudinal axis of conductor 12. Wire 23 is spaced 180° about the longitudinal axis of conductor 12 and therefore is not shown.

Figure 5:
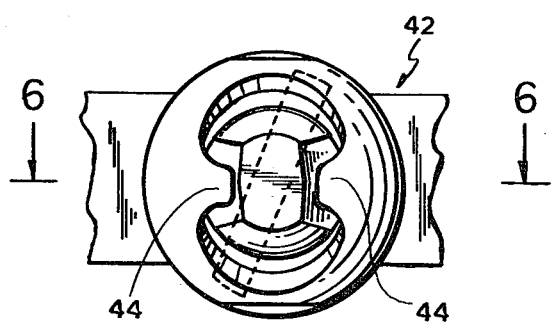
FIG. 5 is a side sectional view of a portion of the bipolar pacing lead after installation of the insulating sheath but before installation of the ring electrode.

FIG. 5 shows the assembly after insulating sheath 10 has been applied. Notice that the inside diameter of insulating sheath 10 is approximately the same as the outside diameter of conductor 12 providing a proper fit. The outside diameter is about 2.1 mm. Insulating sheath 10 is an electrical insulator compatible with the implant environment. Polyurethane is typical material. Because wires 22 and 23 protrude from conductor 12, insulating sheath 10 is stretched along 42 and 44 as shown. Insulating sheath 10 is sufficiently flexible, however, to stretch over wires 22 and 23.

Figure 6:
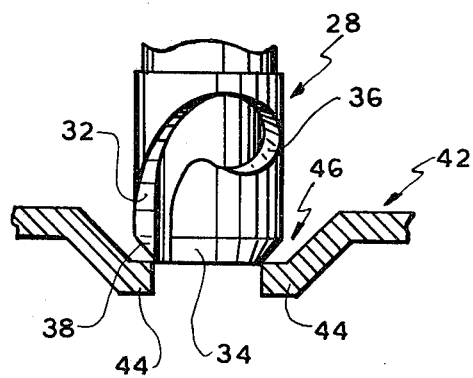
FIG. 6 is a side sectional view after placement of the ring electrode before swaging.

FIG. 6 shows the placement of ring electrode 20 having an inside diameter larger than the outside diameter of insulating sheath 10 and sufficient to permit insertion over the protrusions at 42 and 44. A typical ring electrode is about 6.4 mm in length and made from platinum/iridium. For an insulating sheath of 2.1 mm outside diameter, ring electrode 20 would have an inside diameter of about 2.2 mm and an outside diameter of about 2.4 mm.

Ring electrode 20 is then swaged to an outside diameter of about 2.1 mm (i.e., same as insulating sheath 10) producing the final configuration seen in FIG. 2. Wires 22 and 23 puncture insulating sheath 10 creating punctures 26 and 27. Wires 22 and 23 contact ring electrode 20 along their length to create contact points 30 and 31. The force also creates seal points 46, 47, 48 and 49 between insulating sheath 10 and ring electrode 20.

Figure 7:
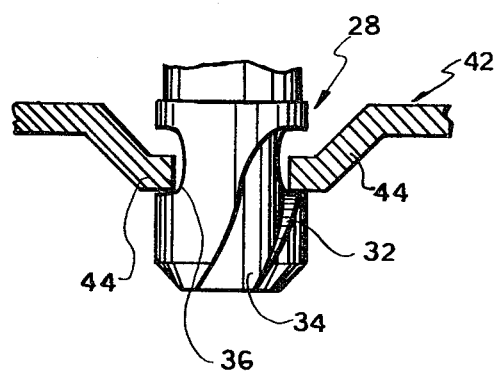
FIG. 7 shows the major fabrication steps.
Figure 3:
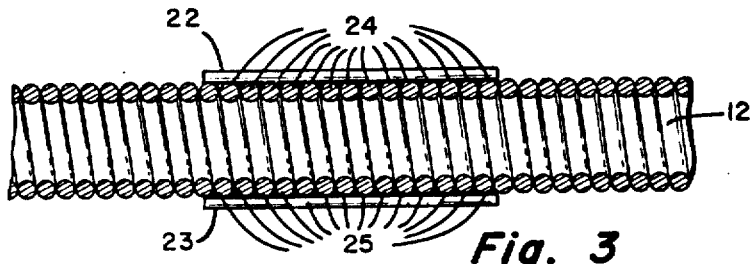
Figure 4:
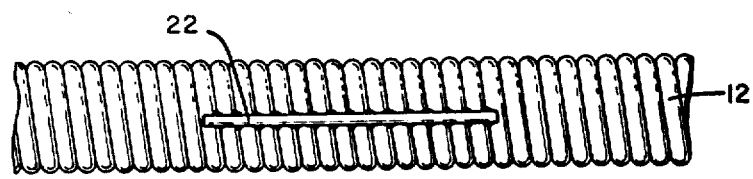
Figure 5:
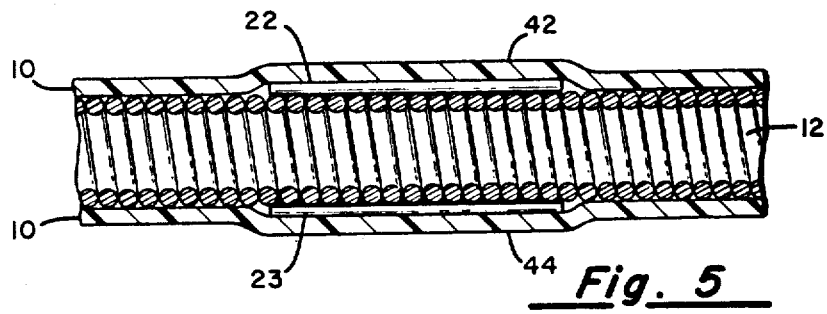
Figure 6:
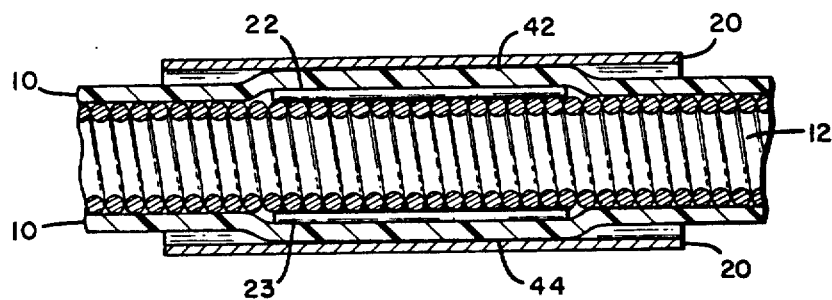

The steps of manufacture are shown in FIG. 7 in chronological order. At element 50 wires 22 and 23 are cut to size. The coils of conductor 12 are welded at element 52 to produce a rigid cylinder. Wires 22 and 23 are welded to conductor 12 at element 54. Insulating sheath 10 is installed at element 56. At element 58 ring electrode 20 is placed into position. The final step at element 60 is swaging ring electrode 20 to its final outside diameter.

From the above description, those of ordinary skill in the art will be able to apply the present invention to situations other than the bipolar pacing lead of the preferred embodiment.

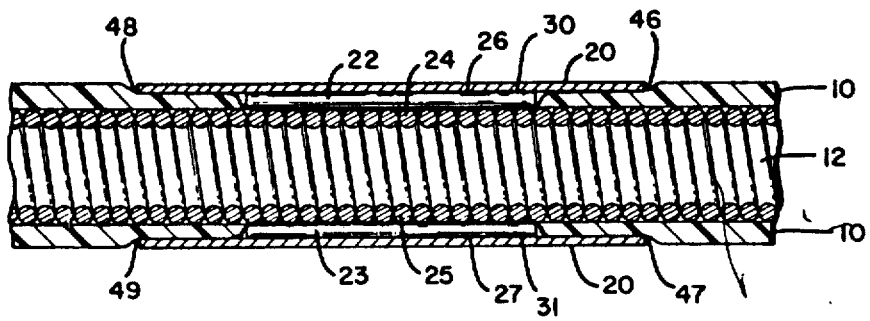

Patent No. 4,381,014 Page 3 of 4
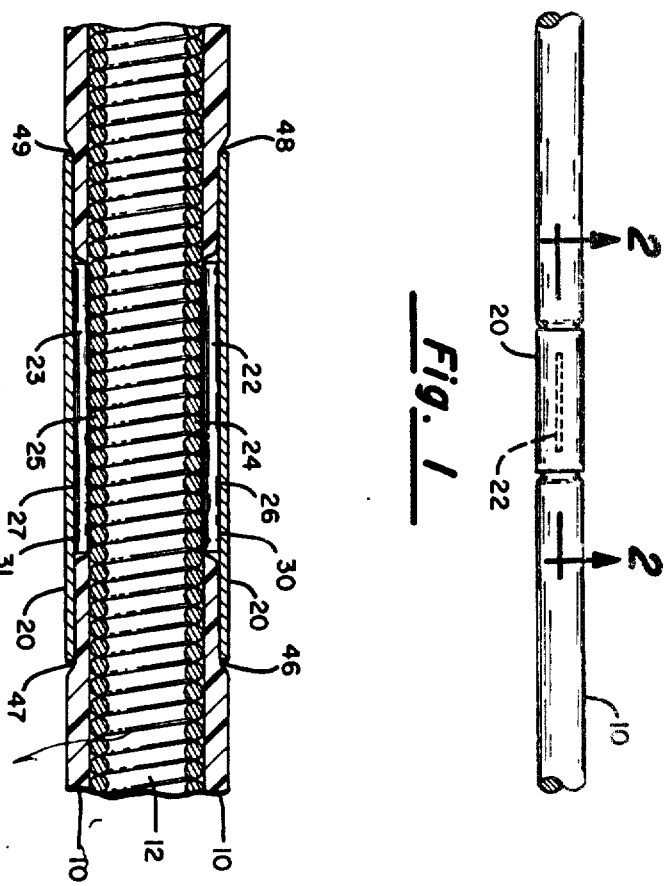
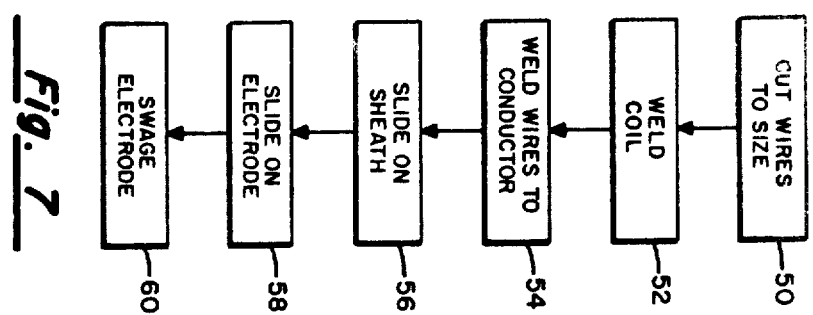

What is claimed is:

1. An electrode for an implantable lead comprising:
   an electrical conductor;
   a continuous insulating sheath;
   conductor means
   means for attaching said conductor means to said electrical conductor; and
   conductive ring of material substantially impervious to body fluids frictionally attached to said conductor means and said continuous insulating sheath.

2. An electrode according to claim 1 wherein said conductor means is at least one wire.

3. An electrode according to claim 2 wherein said at least one wire is a hard metal.

4. An electrode according to claim 3 wherein said attaching means is a weld.

5. An electrode according to claims 1, 2, 3 or 4 wherein said conductive ring is swaged to have approximately the same outside diameter as said continuous insulating sheath.

6. An electrode according to claim 5 wherein said electrical conductor is a coil of wire having coils welded together at the position in which said conductor means is fixedly attached.

7. A method of making a ring electrode for a medical lead having a conductor and a continuous insulating sheath comprising the steps of:
   (a) cutting at least one length of wire shorter than the length of said ring electrode;
   (b) subsequently attaching said wire to said conductor at a position desired for said ring electrode;
   (c) subsequently encasing said conductor in said continuous insulating sheath;
   (d) subsequently sliding a ring shaped conductor of material essentially inert to body fluids over said continuous insulating sheath; and
   (e) subsequently swaging said ring shaped conductor to cause both ends of said at least one length of wire to penetrate said continuous insulating sheath and said ring shaped conductor to be frictionally attached to said continuous insulating sheath.

8. A method according to claim 7 wherein said attaching step further comprises welding.

9. A method according to claim 8 wherein said conductor is a coil of wire, further comprising:
   welding said coil together at said position desired for said ring electrode, prior to said encasing step.

10. A method according to claim 9 wherein said welding further comprises laser welding.

11. A method according to claim 9 wherein said welding further comprises resistive welding.

12. A method according to claims 6, 7, 8 or 9 wherein said swaging step further comprises swaging said ring-shaped conductor until the outside diameter of said ring-shaped conductor is approximately equal to the outside diameter of said continuous insulating sheath.

13. An electrode for an implantable lead comprising:

a coiled electrical conductor further comprised of at least two adjacent coils permanently affixed to one another;

a continuous insulating sheath surrounding the coiled electrical conductor;

conductor means permanently and fixedly attached to said coiled electrical conductor at the location of said at least two adjacent coils and extending through said continuous insulating sheath; and a conductive ring of material substantially impervious to body fluids frictionally attached to said conductor means and to said continuous insulating sheath.

14. An electrode according to claim 13 wherein said at least two adjacent coils are welded together whereby said at least two adjacent coils are permanently affixed to one another.

15. An electrode according to claim 14 wherein said conductor means is at least one wire.

16. An electrode according to claim 15 wherein said conductor means is welded to said coiled electrical conductor.

17. An electrode according to claim 16 wherein said conductive ring is swaged to have approximately the same outside diameter as said continuous insulating sheath, whereby said conductive ring is frictionally attached to said conductor means and to said continuous insulating sheath.

* * * * *

UNITED STATES PATENT AND TRADEMARK OFFICE
CERTIFICATE OF CORRECTION

PATENT NO. : 4,381,014

DATED : April 26, 1983

INVENTOR(S) : Richard D. Sandstrom et al.

It is certified that error appears in the above-identified patent and that said Letters Patent is hereby corrected as shown below:

The title page showing the illustrative figure and Figs. 1, 2 and 3 should be deleted to appear as per attached pages.

Signed and Sealed this

Twentieth Day of September 1983

[SEAL]

Attest:

GERALD J. MOSSINGHOFF

Attesting Officer     Commissioner of Patents and Trademarks

United States Patent [19] [11] 4,381,014
Sandstrom et al. [45] Apr. 26, 1983

[54] RING ELECTRODE FOR PACING LEAD AND METHOD OF MAKING SAME

[75] Inventors: Richard D. Sandstrom, Scandia; Robert G. Dutcher, Columbia Heights; Keith A. Ufford, Maple Grove, all of Minn.

[73] Assignee: Medtronic, Inc., Minneapolis, Minn.

[21] Appl. No.: 195,987

[22] Filed: Oct. 10, 1980

[51] Int. Cl.³ .............................................. A61N 1/04
[52] U.S. Cl. .................................................... 128/786
[58] Field of Search ............... 128/639, 784, 785, 786, 128/419 P

[56] References Cited

U.S. PATENT DOCUMENTS

| | | | |
|---|---|---|---|
| 3,348,548 | 10/1967 | Chardack | 128/419 P |
| 3,568,660 | 3/1971 | Crites | 128/786 |
| 3,837,347 | 9/1974 | Tower | 128/419 P |
| 4,156,429 | 5/1979 | Amundson | 128/419 P |
| 4,280,511 | 7/1981 | O'Neill | 128/784 |

Primary Examiner—William E. Kamm
Attorney, Agent, or Firm—Reed A. Duthler; Joseph F. Breimayer; John L. Rooney

[57] ABSTRACT

A structure for use as an electrode on a pacing lead to be located some distance proximal to the distal end of the pacing lead. Two short lengths of wire having high electrical conductivity are cut to size. The coils of the outer conductor are welded together at the desired location of the ring electrode of the lead. The two short lengths of wire are welded to the outer conductor of the lead at the desired location of the ring electrode. An insulating sheath having an inside diameter close to the outside diameter of the outer conductor is slid over the outer conductor. The flexibility of the insulating sheath is sufficient to permit encasing of the two short lengths of wire, though the insulating sheath is caused to protrude at the two places directly over and corresponding to the two short lengths of wire. A conductive ring having an inside diameter sufficient to permit sliding over the insulating sheath and two points of protrusion is placed around the insulating sheath at the desired location of the ring electrode. The conductive ring is swaged to an outside diameter approximating that of the insulating sheath. The forces produced cause the two short lengths of wire to pierce the insulating sheath and come in contact with the conductive ring which thereby creates an electrically conductive path between the outer conductor and the conductive ring.

17 Claims, 7 Drawing Figures